United States Patent [19]

Gupta

[11] Patent Number: 5,567,853
[45] Date of Patent: Oct. 22, 1996

[54] PURIFICATION OF ACETONE

[75] Inventor: Vijai P. Gupta, Berwyn, Pa.

[73] Assignee: Arco Chemical Technology, L.P., Greenville, Del.

[21] Appl. No.: 526,151

[22] Filed: Feb. 17, 1995

[51] Int. Cl.$^6$ ................................................. C07C 49/04
[52] U.S. Cl. ................................ 568/411; 203/63
[58] Field of Search .................. 568/410, 411; 203/63

[56] References Cited

U.S. PATENT DOCUMENTS

| | | | |
|---|---|---|---|
| 2,624,699 | 1/1953 | Joris | 508/411 |
| 2,906,675 | 9/1959 | Hall et al. | 508/411 |
| 2,906,676 | 9/1959 | Bewley et al. | 508/411 |
| 3,668,256 | 6/1972 | Brundege | 203/51 |
| 4,329,510 | 5/1982 | Uno et al. | 203/51 |
| 4,584,063 | 4/1986 | Berg et al. | 203/51 |
| 4,620,901 | 11/1986 | Berg et al. | 568/411 |

*Primary Examiner*—James H. Reamer
*Attorney, Agent, or Firm*—William C. Long

[57] ABSTRACT

Acetone produced during MTBE production and containing methanol, aldehydes and other organic impurities is contacted with a solution of basic material such as NaOH in lower glycol at conditions effective to polymerize aldehyde impurities, the polymerized impurities are separated, and acetone is separated from methanol in an extractive distillation using the same lower glycol as extractive distillation agent.

7 Claims, 1 Drawing Sheet

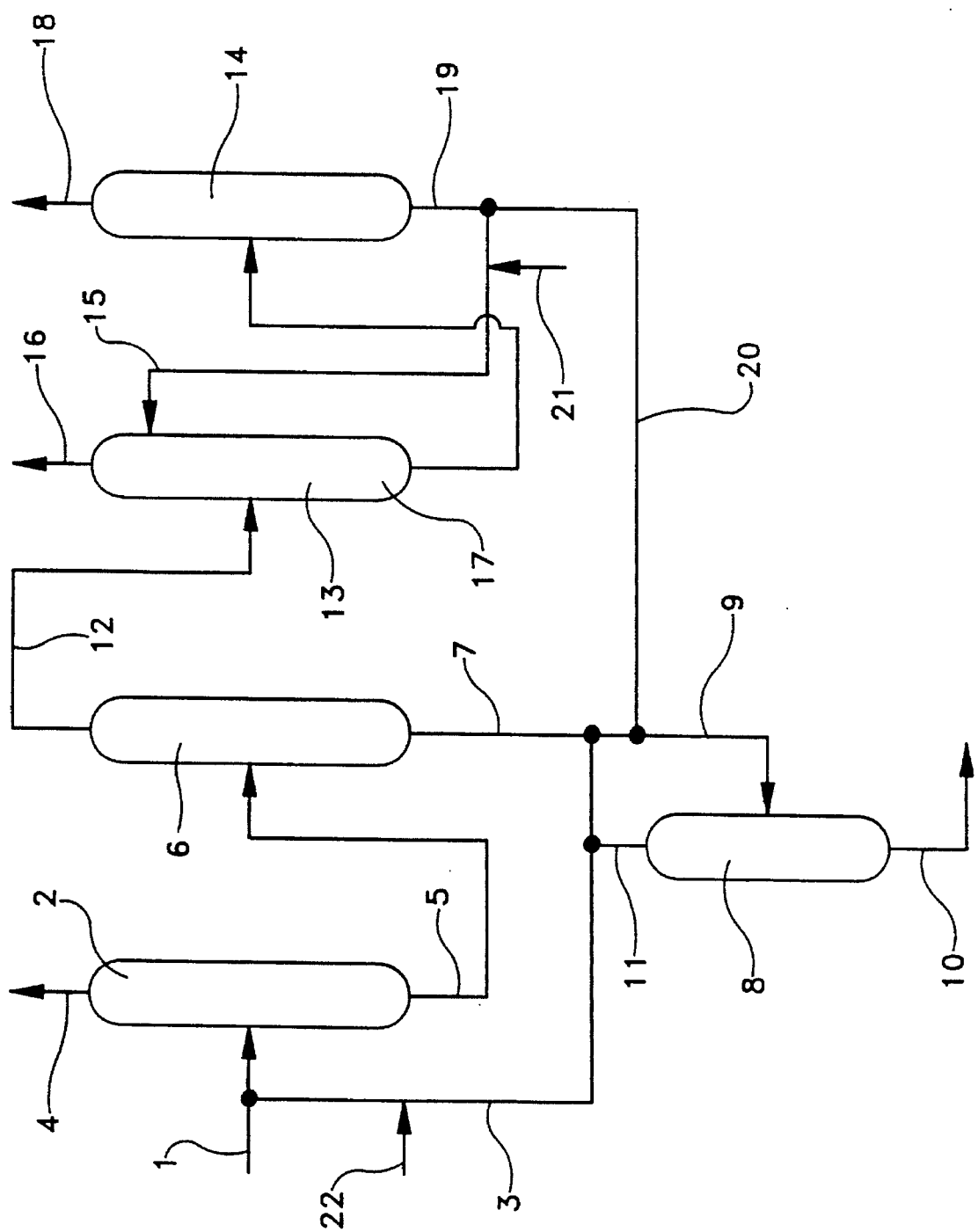

PURIFICATION OF ACETONE

BACKGROUND OF THE INVENTION

1. Field of the Invention

The present invention relates to the separation of acetone from methanol and aldehyde impurities by treatment with a basic material and a lower glycol.

2. Description of the Prior Art

Methyl tertiary butyl ether (MTBE) is an important industrial chemical useful, for example, as a fuel additive. In commercial practice, MTBE is produced by the reaction of methanol with isobutylene and/or tertiary butyl alcohol. An important source of the isobutylene and/or tertiary butyl alcohol is from the Oxirane process which is widely practiced commercially for the coproduction of propylene oxide and tertiary butyl alcohol. The isobutylene and/or tertiary butyl alcohol produced from the Oxirane process tends to also contain oxygenated impurities such as acetone and methanol as well as aldehydes.

While the bulk of the acetone can be separated by distillation, the resultant acetone fraction is contaminated with methanol which forms an azeotrope with acetone as well as with close boiling aldehydes such as butyraldehydes with acids such as butyric acid, and with impurities such as methyl ethyl ketone, tertiary butyl alcohol, MTBE and the like which form azeotropes with water.

It has previously been known to separate aldehyde impurities from acetone by treatment with aqueous caustic or with solid caustic. See U.S. Pat. Nos. 2,624,699, 2,906,675, 2,906,676, 3,668,256 and 4,329,510, for example. Such prior techniques are not, however, satisfactorily applied to acetone derived from the Oxirane process. The use of solid caustic causes the formation of excessive heavy material while the use of aqueous caustic results in the introduction of water which cannot be readily removed due to the formation of low boiling azeotropes with various impurities associated with the acetone.

It has been suggested in the prior art that mixtures of methanol and acetone can be separated by extractive distillation using various agents including lower glycols as extractive distillation agents. See U.S. Pat. No. 4,584,063.

SUMMARY OF THE INVENTION

In accordance with the present invention, acetone containing impurities as above described can be readily purified by contact with a solution of an alkali metal compound in a lower glycol. This contact results in the polymerization of aldehyde impurities to readily separable heavies and neutralization of any acid impurities while the lower glycol is used to separate methanol from the acetone by extractive distillation.

BRIEF DESCRIPTION OF THE DRAWING

The attached drawing is a schematic representation of an embodiment of the invention.

DETAILED DESCRIPTION

The invention can best be described with reference to the attached drawing. Referring to the drawing, impure acetone produced in the Oxirane propylene oxide and tertiary butyl alcohol process is introduced via line 1 to distillation zone 2. The impure acetone generally comprises by weight about 70 to 90% acetone, 3 to 18% methanol, 0.01 to 3% aldehyde, and the balance impurities such as methyl ethyl ketone (MEK), tertiary butyl alcohol (TBA) and MTBE. Also introduced via line 3 to zone 2 in combination with the impure acetone is a solution of an alkali metal compound such as NaOH or Na methylate in propylene glycol. Ethylene glycol can be used in place of the propylene glycol. Sodium methylate can be used as a solution in methanol which is diluted into the glycol. Generally, dilute solutions of basic compound in the glycol are employed, e.g. 1 to 20 wt % NaOH or Na methylate or the like in the glycol.

In distillation column 2, light impurities are distilled overhead via line 4 from the impure acetone and basic containing glycol solution which is removed via line 5 and passed to distillation column 6. In columns 2 and 6, the basic material catalyzes the polymerization of aldehyde impurities to higher boiling materials, and a bottoms stream comprised of the basic material, glycol, and the polymerized higher boiling impurities is removed via line 7. Some of this bottoms stream is recycled via line 3 to distillation zone 2 with a portion passing to stripper 8 via line 9. In stripper 8, glycol is stripped from the basic material and organic heavies, these latter materials being purged via line 10 and the stripped glycol being recycled via lines 11 and 3 to distillation zone 2.

A stream comprised of methanol, acetone, and other impurities such as tertiary butyl alcohol which is substantially free of aldehyde impurities is passed from column 6 via line 12 to extractive distillation column 13. Glycol extractive distillation agent from stripper 14 is passed to column 13 via line 15. In extractive distillation column 13, methanol and other oxygenated impurities such as tertiary butyl alcohol, isopropyl alcohol, and methyl ethyl ketone are separated from acetone by the extractive distillation, purified acetone substantially free both of methanol and aldehyde impurities being recovered via line 16.

The higher boiling methanol with other impurities and propylene glycol mixture passes from column 13 via line 17 to stripper 14 wherein methanol and other impurities are stripped from the propylene glycol and separated via line 18. Propylene glycol is removed via line 19 with a major portion passing via line 15 to column 13 as above described and a small purge being sent via line 20 and line 9 to stripper 8.

Make-up propylene glycol is introduced via line 21 as needed and make-up basic material is introduced as needed via line 22 to the propylene glycol stream passing to column 2 via line 3.

Through practice of the invention, impure acetone derived from the Oxirane propylene oxide process is efficiently separated from aldehyde impurities and methanol without excessive heavies formation and acetone loss. In addition, contamination of the acetone with water as a result of the formation of azeotropes of organic impurities with water is avoided. Water not only presents an acetone contamination problem as when aqueous caustic is used but also would be likely to go overhead in column 6 causing caustic precipitation unless undesirable large water excesses were used as well as energy loss. Use of basic material in lower glycol as provided in accordance with the invention avoids such problems. Conventional equipment and conditions are employed in successful practice of the invention.

The following example illustrates practice of an embodiment of the invention.

The acetone to be purified is a product derived the Oxirane process and comprises by weight 83% acetone, 8% methanol, 1% aldehyde which are mainly butyraldehydes, and 8% close boiling organic impurities.

Referring to the accompanying drawing, the impure acetone in amount of 960 lbs/hr is combined with 40 lbs/hr of a sodium hydroxide in propylene glycol solution (10 wt % NaOH) via lines 22 and 3.

In column 2, light boiling materials are removed overhead via line 4 at 58° C. and 5 psig at the rate of 60 lbs/hr.

The acetone containing bottoms at 69° C. and 7 psig passes via line 5 to column 6 wherein acetone is separated from polymerized aldehyde impurities. An overhead acetone containing stream is removed via line 12 at 65° C. and 5 psig and passes at the rate of 880 lbs/hr to extractive distillation column 13. This stream comprises by weight about 86% acetone, 7 methanol, and 7% other organics.

A heavies stream is passed from column 6 via lines 7 and 9 to stripper 8 at 120° C. and 11 psig at the rate of 60 lbs/hr. This stream comprises by weight 7% caustic, 67% propylene glycol and 26% heavy organics, including aldehyde polymers. It is combined with about 20 lbs/hr of the glycol purge from line 20 and introduced to stripper 8 wherein at 116° C. and 50 mmHg 25 lbs/hr of propylene glycol is stripped overhead and recycled via lines 11 and 3.

A caustic and heavy organic stream is purged at the rate of 55 lbs/hr via line 10.

In extractive distillation column 13, separation of acetone from methanol and propylene glycol takes place. Propylene glycol at the rate of 1,740 lbs/hr is introduced into the upper section of column 13 via line 15. A purified acetone product stream is removed from zone 13 via line 16 at the rate of 750 lbs/hr, at 65° C. and 5 psig. This stream comprises by weight 98.3% acetone, 1.4% methanol and 0.3% other materials. It can be further purified by conventional distillation to reduce the content of methanol and other impurities.

A bottoms stream at 159° C. and 11 psig passes at the rate of 1,870 lbs/hr via line 17 to stripper 14. A crude methanol stream at 70° C. and 2 psig is recovered via line 18 at the rate of 130 lbs/hr. This stream comprises by weight 41% methanol, 14% acetone, and 45% others. A bottoms propylene glycol stream is removed at the rate of 1,740 lbs/hr at 197° C. and 5 psig via line 19, 1,720 lbs/hr being recycled via line 15 to column 13. The remaining propylene glycol, 20 lbs/hr, is sent to stripper 8 via line 20. Make-up propylene glycol is added via line 21 at the rate of 20 lbs/hr.

It will be apparent from the above that practice of the invention provides a convenient and exceedingly effective process for the purification of acetone which contains methanol, aldehyde and other close boiling organics.

Preferred basic materials employed are NaOH or Na methylate or the corresponding potassium compounds although other compounds can be used if desired. The use of aqueous basic materials is not feasible because the added water tends to azeotrope with various organic impurities.

In addition to the important purification feature of the invention, practice of the invention results in neutralization of acidic materials thus enabling use of mild steel equipment with a sizable economic benefit.

I claim:

1. The method for the separation of methanol and aldehyde impurities from acetone which comprises contacting the impure acetone with a solution of a catalytic amount of a sodium or potassium compound in ethylene glycol or propylene glycol at conditions of elevated temperature effective to polymerize the aldehyde impurities, separating the polymerized aldehyde impurities by distillation from an acetone and methanol mixture, and separating purified acetone from the methanol by extractive distillation using the said glycol as extractive distillation solvent.

2. The method of claim 1 wherein the glycol is propylene glycol.

3. The method of claim 1 wherein the glycol is ethylene glycol.

4. The method of claim 1 wherein the sodium or potassium compound is NaOH.

5. The method of claim 1 wherein the sodium or potassium compound is KOH.

6. The method of claim 1 wherein the sodium or potassium compound is Na methylate.

7. The method of claim 1 wherein the sodium or potassium compound is K methylate.

* * * * *